United States Patent
Jones et al.

(10) Patent No.: US 9,134,225 B2
(45) Date of Patent: Sep. 15, 2015

(54) ADDITIVE PHOTOMETRIC ANALYSIS

(75) Inventors: Christopher M. Jones, Houston, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 856 days.

(21) Appl. No.: 13/386,369

(22) PCT Filed: Aug. 14, 2009

(86) PCT No.: PCT/US2009/053846
§ 371 (c)(1),
(2), (4) Date: May 16, 2012

(87) PCT Pub. No.: WO2011/019355
PCT Pub. Date: Feb. 17, 2011

(65) Prior Publication Data
US 2012/0232707 A1    Sep. 13, 2012

(51) Int. Cl.
G01N 21/31    (2006.01)
G01N 21/27    (2006.01)
G01N 21/85    (2006.01)

(52) U.S. Cl.
CPC .............. *G01N 21/31* (2013.01); *G01N 21/274* (2013.01); *G01N 21/85* (2013.01); *G01N 2201/1293* (2013.01)

(58) Field of Classification Search
USPC .............. 700/200, 201, 283; 702/32; 96/176, 96/216; 210/188; 422/81–82
See application file for complete search history.

(56) References Cited

U.S. PATENT DOCUMENTS

| | | | |
|---|---|---|---|
| 6,386,014 B1 * | 5/2002 | Butch | 73/23.35 |
| 6,568,911 B1 * | 5/2003 | Brightwell et al. | 417/53 |
| 7,833,489 B2 * | 11/2010 | Chen | 422/528 |
| 8,349,074 B2 * | 1/2013 | Ohtsuna et al. | 117/15 |
| 2004/0069942 A1 | 4/2004 | Fujisawa et al. | |
| 2005/0265905 A1 | 12/2005 | Young | |
| 2006/0142955 A1 | 6/2006 | Jones et al. | |

(Continued)

FOREIGN PATENT DOCUMENTS

| AU | 2009351116 B2 | 2/2014 |
|---|---|---|
| EP | 0678742 | 7/2002 |
| WO | WO-20110019355 A2 | 2/2011 |

OTHER PUBLICATIONS

"Australian Application Serial No. 2009351116, First Examiner Report mailed Jan. 22, 2013", 2 pgs.

(Continued)

*Primary Examiner* — Kidest Bahta
(74) *Attorney, Agent, or Firm* — Schwegman Lundberg & Woessner, P.A.; Benjamin Fite (57) ABSTRACT

Apparatus, systems, and methods may operate to discharge a plurality of spike fluids into a fluid flowing in a flow channel, transmit energy to the fluid using an energy source coupled to the flow channel, receive the energy modified by the fluid as photometric energy, convert the photometric energy to at least one photometric signal, compare the at least one photometric signal with a reference signal to determine at least one photometric property of the fluid, and determine at least one component of the fluid using the at least one photometric property supplied to a generalized standard addition method (GSAM). Additional apparatus, systems, and methods, including the use of multivariate curve resolution (MCR) to refine GSAM results, are disclosed.

26 Claims, 7 Drawing Sheets

(56) References Cited

U.S. PATENT DOCUMENTS

2006/0169030 A1 8/2006 Stewart et al.
2007/0258319 A1 11/2007 Ronnekleiv et al.

OTHER PUBLICATIONS

"Australian Application Serial No. 2009351116, Response filed Sep. 6, 2013 to Examiner's Report mailed Feb. 22, 2013", 2 pgs.

"Australian Application Serial No. 2009351116, Subsequent Examiners Report mailed Sep. 26, 2013", 3 pgs.

"European Application 09848337.3, European Search Report mailed Dec. 21, 2012", 5 pgs.

"European Application 09348337,3, Office Action mailed Jan. 8, 2013", 1 pg.

"European Application 09848337.3, Response filed Jul. 11, 2013 to Office Action mailed Jan. 8, 2013 and European Search Report mailed Dec. 21, 2012", 12 pgs.

Saxberg, B. E. H., et al., "Generalized Standard Addition Method", *Analytical Chemistry*, 51(7), (Jun. 1979), 1031-1038.

Tyson, J. F., et al., "Flow Injection Calibration Methods for Atomic Absorption Spectrometry", *Analytica Chimca Acta*, 145, (1983), 159-168.

"International Application Serial No. PCT/US09/53846, Search Report mailed Oct. 8, 2009".

"International Application Serial No. PCT/US09/53846, Written Opinion mailed Oct. 8, 2009".

"Malaysian Application Serial No. PI 2012000417, Response filed Jun. 17, 2014 to Examination Report mailed May 15, 2014", 6 pgs.

"Malaysian Application Serial No. PI 2012000417, Examination Report mailed May 15, 2014", 3 pgs.

"International Application Serial No. PCT/US2009/53846, International Preliminary Report on Patentability mailed May 1, 2012", 4 pgs.

"Australian Application Serial No. 2009351116, Response filed Jan. 17, 2014 to Examiners Report mailed Sep. 26, 2013", 18 pgs.

"International Application Serial No. PCT/US09/53846, Response filed Feb. 26, 2010 to Written Opinion mailed Oct. 8, 2009", 4 pgs.

"European Application Serial No. 09848337.3, Examination Notification Art. 94(3) mailed Jun. 5, 2015", 6 pgs.

* cited by examiner

ADDITIVE PHOTOMETRIC ANALYSIS

RELATED APPLICATIONS

This application is a U.S. National Stage Filing under 35 U.S.C. 371 from International Application No. PCT/US2009/053846, filed on Aug. 14, 2009, and published as WO 2011/019355 A1 on Feb. 17, 2011; which application and publication are incorporated herein by reference in their entirety.

BACKGROUND

Spectroscopic analysis conducted in a down hole environment is subject to several drawbacks. The first involves the typical conditions imposed on the instrumentation, namely: high temperature, high pressure, and lots of vibration. The second is that the composition of fluid being analyzed often varies a great deal with temperature and pressure. Finally, spectral signals received from the fluid components tend to be rather broad, so that relatively few discrete component signals in the complex mixture can be isolated, leading to a high level of interference. To compound this latter problem, the most common method of dealing with harsh conditions down hole is to use spectroscopic analysis components that are robust, but inherently sensitive to multiple interferents. In summary, spectroscopic fluid analysis down hole does not lend itself to discrete analysis, the choice of spectroscopic components can magnify the problem, and even when these limitations are overcome, the matrix dependent response of the fluid can change dramatically when environmental conditions change.

DETAILED DESCRIPTION

To overcome some of the difficulties posed by spectroscopy conducted in a down hole environment, some operators have attempted to perform chemometric multivariate calibration for a large number of fluid samples prior to conducting a down hole analysis. This approach may entail taking thousands of fluid sample measurements that span the range of compositions to be observed down hole, as well as the expected range of temperature and pressure. Providing surface calibration measurements that accurately reproduce the matrix of fluids to be observed down hole is difficult. The difficulty may be increased if the optical component (including light source and detector) operational characteristics also depend on conditions down hole.

Although multivariate calibration techniques (e.g., principal component regression) are useful for mitigating matrix effects, the regression tends to fail when an uncalibrated matrix is observed. And since it is improbable that the specific matrix observed down hole will be reproduced in its entirety at the surface, the resulting interpolation/extrapolation is very likely to degrade the regression.

This degradation may be amplified by the nonlinear characteristics of most fluid matrices. Although nonlinear multivariate calibration techniques exist, the calibration matrix mapping used in these techniques is orders of magnitude more complex than what suffices for linear multivariate techniques.

Over a smaller range of matrix effects, as with any "curve" (or multidimensional surface in the case reservoir fluid spectral factors), the behavior of the fluid matrix is approximately linear. However, to effectively implement this assumption, reservoir fluids analyzed in down hole environments should be properly classified according to the matrix type. Improper classification, or lack of a matching matrix, can also be detrimental to the regression.

Matrix classification is performed on raw spectroscopic responses. The process can be robust for high resolution spectroscopic data. However, it's effectiveness is limited when low resolution spectroscopic data provided by low resolution down hole spectroscopic components is used.

The problem becomes one of degrees of freedom. There are essentially more matrix classes than there are available orthogonal spectroscopic signals. Information from other sensors, or some a priori knowledge of the fluid matrix is then needed in addition to what is provided by the raw spectroscopic sensors. Even if the choice for matrix classes can be narrowed, the number of spectroscopic signals (e.g., six to eight) does not usually offer enough data for sufficient overdetermination of the system in the way of classification.

One potential solution for these difficulties resides in using the generalized standard addition method (GSAM) technique. GSAM is related to the standard addition method (SAM) in that the calibration of an analysis takes place substantially simultaneously with the regression.

As part of SAM activity, one of the analytes to be measured is added incrementally as a "spike" to a sample to be analyzed. With each incremental addition of an analyte, analyte-specific sensors operating on the sample change their response. The change in response is related to the known spike concentration, and the response curve is directly related to the response of the spike-free fluid as the intercept of the response to the slope of the response. The final spiked concentrations of analyte are generally held to less than 10% of the original spike-free concentration of the analyte.

The process of spiking with low analyte concentration ensures that the composition portion of the fluid matrix remains substantially unchanged. Slight matrix-dependent nonlinear behavior can often be modeled with a higher order linear equation, and solved as the intercept/derivative of the curve at zero spike concentration. Additionally, because the sensors make the measurement for calibration and regression simultaneously, it is not necessary to characterize the sensors with respect to system dependence (e.g., sensor response changes as a factor of time or particle buildup). Unfortunately, the analyte-specific sensors used in SAM can lead to another set of problems.

For example, when an inteferent exists that causes a response in one of the analyte-specific sensors, the initial spike-free response of the sample is not truly known. No additional information for a single analyte spike series is available to separate the response of the analyte and inteferent. If all inteferents for a particular analyte are known, then a response factor for the sensor versus inteferent and analyte can be built as part of the SAM technique. Yet, this process alone does not provide the information needed to determine the original concentration of the analyte in the sampled fluid mixture.

However, if a number of non-specific sensors are provided, each with an orthogonal response factor with respect to the analyte and inteferent, then in combination with SAM techniques enough information to solve for the concentration of analyte and inteferent is available. This approach can be implemented via a system of linear equations if the system is exactly determined, or via an inversion if the system is overdetermined. To resolve the analyte in this fashion general makes use of a priori knowledge about the set of potential inteferents, a large number of standard addition operations, and a set of orthogonally selective sensors.

Via the generalized inverse method, the GSAM provides an estimate of the analytes of interest so long as the number of additions is equal to or greater than the number of analytes plus inteferents, and so long as the number of sensors are equal to or greater than the number of analytes plus inteferents. It should be noted that no degrees of freedom are lost in the matrix correction.

This approach can be advantageous when the number of sensors is small, since the number of matrix effects plus analytes plus inteferents may quickly lead to an underdetermined system. It also has the advantage that the inteferent concentration need not be known, so long as the inteferent concentration in the standard addition set changes. GSAM also has the advantage that the number of additions may be much lower than the SAM method while still taking advantage of the SAM benefits.

For example, as a rough proxy, oil may be considered to consist essentially of saturates, aromatics, resins, and asphaltenes (SARA). The saturates may further be broken down according to paraffins, isoprenoids, and napthenes. The aromatics, resins, and asphaltenes may also be broken down into about three subcategories each.

The oil may alternatively be broken down into distillate sections—usually on the order of eight. The distillate distribution of oil includes composition due to the light ends fraction, gasoline fraction, diesel fraction etc. Other non-oil fractions of the fluid may include $CO_2$, $H_2O$, $H_2S$, etc.

There are about 20 classes of compounds that define the fluid matrix of crude oil. For every 10% change in the concentration of these components, a new matrix may be defined. Because the number of possible combinations that operate to redefine the matrix is quite large, the process of calibrating analytes for all of the potential combinations can be difficult. When the variability of the sensors themselves in any given environment (e.g., temperature, pressure, vibration, etc.) is also considered, reliably predicting fluid composition can become very difficult indeed. However, GSAM techniques can be employed in many instances to enable calibration of instrumentation within a variety of environments, over a large number of fluid matrices, in a practical way.

Consider the following example. Assume that a small spike of a single fluid is injected into a moving fluid stream. A sensor located in the fluid stream responds to a common component of the flowing fluid and the spike sample, providing a change in its response to the component as a function of time while the diluted spike moves past the sensor. Knowing the spike volume and the volumetric flow rate of the fluid, including the spike, provides enough information to normalize the time profile of the sensor response to a concentration profile. That is, the total area under the response curve is equal to the total volume of the spike, with the volume of fluid over which the spike response occurs taken as the concentration profile for that spike response.

In a classical sense, by assuming that the original fluid prior to spike addition is homogenous over the spike duration, the concentration profile that results comprises a classical SAM profile. In some embodiments, homogeneity is forced by pushing the fluid, which may comprise a formation fluid, through a porous medium.

In the GSAM method multiple spikes are added to the fluid sample in an additive manner. If multiple spikes of different compositional fluids are added to the moving fluid over a short distance, then, as the spike profiles of the individual samples broaden with time, the individual spike concentrations will vary in the original fluid with respect to distance. If multiple non-specific sensors are used to detect the fluid response over a relatively short distance, then the sensor responses can be considered to measure the characteristics of substantially the same fluid as it moves past. As the individual spike can be normalized to a concentration profile in an unvarying sense, the response matrix of a sensor array may be used to determine the concentration profile of the overlapping (and concentration varying) multiple-spiked fluid.

The response profile of the fluid matrix may be inverted through one of the chemometric inversion algorithms that fall into the class of multivariate curve resolution (MCR). Algorithms of this class include, but are not limited to generalized MCR, time evolved factor analysis, and trilinear decomposition. With knowledge of the spike fluid composition, and the concentration profiles of the spike over a short (homogenous) distance within the fluid, the GSAM method may be applied to the concentration profiles to determine the matrix free response factors for the unspiked fluid. The response factor matrix may then be applied to additional unspiked fluid as it moves past the sensor to determine the concentration of discrete or pseudo-component concentrations within the fluid. In the concentration domain, as fluid composition changes are measured by the sensors, the down hole GSAM procedure may be repeated to include a number of cycles as the composition of the fluid approaches the threshold for matrix change.

For example, during a pump out operation, the fluid composition can change grades between two end members (e.g., between contamination and formation fluid). As the composition changes grades, the mixed fluid may cross between a number of matrices, such as 100% contamination, 90% contamination, . . . , 10% contamination, and finally less than 10% contamination. GSAM operations may be repeated a number of times throughout this process to calibrate fluid responses to the sensors as the fluid approaches the threshold for a matrix change.

In the signal domain, a lack of fit parameter may indicate that a new component has been introduced to the system, or that the matrix has changed due to a concentration unrelated factor (e.g., temperature or pressure). In this case, external decision making information, such as the temperature and pressure of the fluid, may indicate additional cycles of that the down hole GSAM method should be applied. For example, if the change in response occurs relatively quickly, a new response factor matrix for the sensor array, as determined by a renewed GSAM application, may be used with data collected prior to the GSAM, up to the point of the "instantaneous" or rapid change. If the change occurs smoothly, however, then the response factors of the GSAM may be interpolated between subsequent GSAM applications.

Certain types of sensors, when combined with GSAM spectroscopy, may afford additional advantages. For example, the response of optical sensors can be very quick (on the order of micro to milliseconds), giving high resolution response profiles for the spiked fluid over short distances. In addition, arrays of optical sensors may contain many individual orthogonal sensors.

Thus, in some embodiments, the effective number of sensors may be increased in a multiplicative fashion by crossing the light source with the detectors. For example, if one assumes that a charge-coupled device (CCD) imaging chip has four different types of detectors (e.g., red, blue, green and white), then interacting light from eight visible wavelength light emitting diodes with orthogonal wave functions effectively provides 32 optical sensors. Because different CCD detectors often have different response curves (e.g., cyan, magenta, yellow, white), the effective sensor number of sensors derived from eight light-emitting diodes (LEDs) and two CCD detectors may total 64 if the white detectors in each of the two CCDs are orthogonal, or 56 if they are not. Because not all detector responses overlap with the energy sources, the number of effective sensors may be reduced from the theoretical maximum.

For example, if a system includes eight orthogonal light sources, and eight orthogonal detectors, the theoretical sensor array comprises 64 channels. However, if some of the detectors do not respond to some light source types (e.g., a mostly red detector in conjunction with a mostly blue light source) then the effective number of channels of the sensor array will be reduced from the theoretical maximum of (in this case) 64 channels.

If the fluid flowing in a channel can be temperature-controlled, then it may be possible to use low-power spectrometers (e.g., 40 C and ~2.5 mW) as the sensors. These devices can provide high resolution data over a range of about 175 nm (e.g., UV) to about 2500 nm (e.g., near or mid infra-red). In some cases, passive evaporative cooling and/or thermo-sonic cooling may be applied. Thus, many embodiments may be realized.

Figure 1:
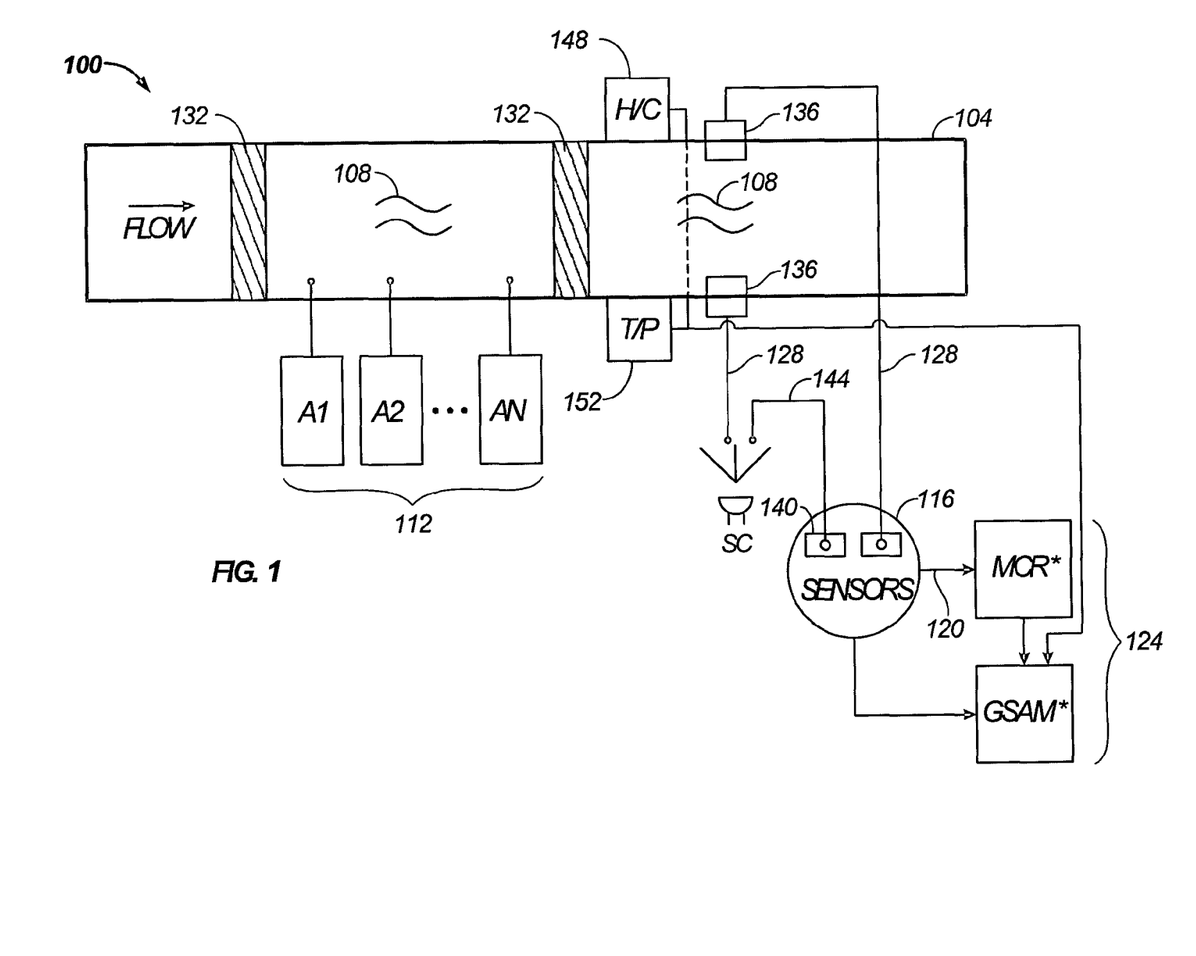
FIG. 1 illustrates a block diagram of an apparatus according to various embodiments of the invention.

For example, FIG. 1 illustrates a block diagram of an apparatus 100 according to various embodiments of the invention. Here it can be seen that an apparatus 100 that can be used to apply GSAM techniques to analyzing a fluid 108 in motion, comprises a flow channel 104 to contain a flow of fluid 108. The apparatus 100 may further include a plurality of fluid injectors 112 to discharge a corresponding plurality of spike fluids A1 ... AN into the flow channel 104.

The apparatus 100 may also include one or more energy sources SC coupled (e.g., optically coupled) to the flow channel 104 to direct energy into the fluid 108, as well as one or more sensors 116 (e.g., optical sensors) coupled to the flow channel 104 downstream from the plurality of fluid injectors 112. The sensors 116 can be used to receive the energy modified by the fluid 108 as photometric energy, providing one or more signals 120 indicating a property of the photometric energy. A "property of the photometric energy" may comprise an amplitude, frequency, or modulation of the signals 120, among others.

The apparatus 100 may also include one or more processors 124. For example, the apparatus 100 may include a processor GSAM* to acquire the signals 120 and determine a material or chemical property of the fluid 108 using the GSAM applied to the signals 120. Prior to GSAM processing, or at about the same time, the apparatus 100 may also operate to apply MCR to the signals 120 via the processor MCR*.

Thus, in an elementary form, the apparatus 100 may comprise several sensors 116 arranged as an array (shown in FIG. 1), where the source SC and sensors 116 are indirectly coupled to the channel 104, perhaps using optical fibers 128 and optical ports 136 disposed around the outside of the flow channel 104. The sensors 116 can be used to monitor the photometric response of the fluid 108 after the fluid injectors 112 discharge standard fluid spikes into the fluid 108. In some embodiments, the sensors 116 are directly coupled to the channel 104 (e.g., sensors 116 mounted in the walls of the channel 104), so that no medium is used to communicate between the interior of the channel 104 and the sensors 116.

Many variations may be realized. For example, the apparatus 100 may comprise one or more porous media 132 to mix the fluid. Porous media 132 may be disposed within the flow channel 104 downstream and/or upstream from the plurality of fluid injectors 112.

The energy source SC may comprise a variety of types. For example, the energy source SC may comprise one or more broadband energy sources, or one or more substantially monochromatic sources. The energy imparted to the fluid 108 may comprise a plurality of energies (e.g., the energy contained in a number of wavelengths provided by a broadband source, or the energy contained in a discrete set of wavelengths provided by plural, substantially monochromatic sources).

The energy source SC may comprise a number of visible wavelength emission devices. Thus, in some embodiments, the energy source SC comprises one or more LEDs.

In a similar manner, the sensors 116 may comprise a variety of types. For example, a sensor 116 may comprise one of a tunable sensor to resolve a plurality of wavelengths in the photometric energy provided by the fluid 108, or a plurality of sensors corresponding to a plurality of reception wavelength sensitivities. In this way, a plurality of energies can be received in a modified form by a single, tunable sensor 116, or a corresponding plurality of sensors 116. The sensors 116 may also comprise sensors of different types in the same array, or be divided up into separate devices, so that the end result is an effective total number of sensors that is equivalent to multiplying a first number/type of sensor by a second number/type of sensor, as described above.

The sensors 116 may comprise liquid crystal diode (LCD) elements; CCD elements; complementary metal-oxide semiconductor (CMOS) elements; band-gap, silicon, and/or infrared photodiodes; thermal detectors; and combinations of these, among others. Optical fibers 128 may be used to couple the sensors 116 to one or more optical ports 136 in the flow channel 104.

In some embodiments, the GSAM process can incorporate input from a reference. Thus, the apparatus 100 may include one or more sensors 116 to receive the energy (e.g., reference sensors to receive energy from the source SC) unmodified by interaction with the fluid 108. For example, the apparatus 100 may comprise reference detectors 140 and a bypass fiber 144 to couple the energy source SC to the reference detectors 140. The reference detectors 140 can be combined with the main banks of sensors 116, or kept apart from them.

In some embodiments, the apparatus 100 comprises one or more heating and/or cooling devices 148 to control the temperature of the fluid 108 contained in the flow channel 104. The apparatus 100 may also comprise one or more pressure and/or temperature indicators 152 to indicate a fluid matrix condition that initiates application of a revised response factor matrix as part of the GSAM.

Figure 2:
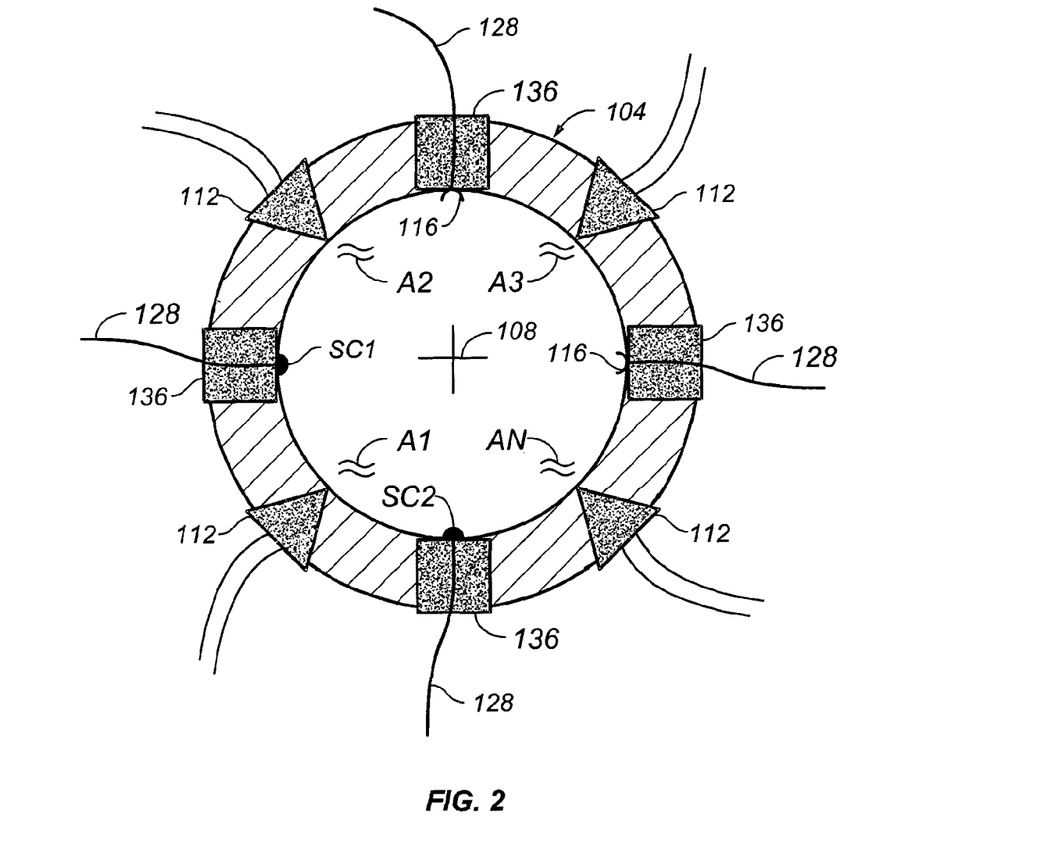
FIG. 2 illustrates an end, cut-away view of a flow channel according to various embodiments of the invention.

FIG. 2 illustrates an end, cut-away view of a flow channel 104 according to various embodiments of the invention. Here it can be seen that the flow channel includes a plurality of energy sources SC1, SC2 and corresponding sensors 116 disposed in a substantially radial arrangement around a periphery of the flow channel 104. As shown in this figure, the energy sources SC1, SC2 and sensors 116 may be mounted directly in the channel. If optical ports 136 are used, the energy sources SC1, SC2 and sensors 116 may be mounted outside the channel 104, perhaps on the other side of the optical ports 136 (not shown). The sources SC1, SC2 and sensors 116 may also be coupled to the channel 104 using optical fibers 128, if desired.

The spike fluid injectors 112 may also be mounted in a substantially radial arrangement around a periphery of the flow channel 104. In some embodiments, the spike fluid injectors 112 are mounted in a linear arrangement, in line with the flow of the fluid 108. Thus, many embodiments may be realized.

Figure 3:
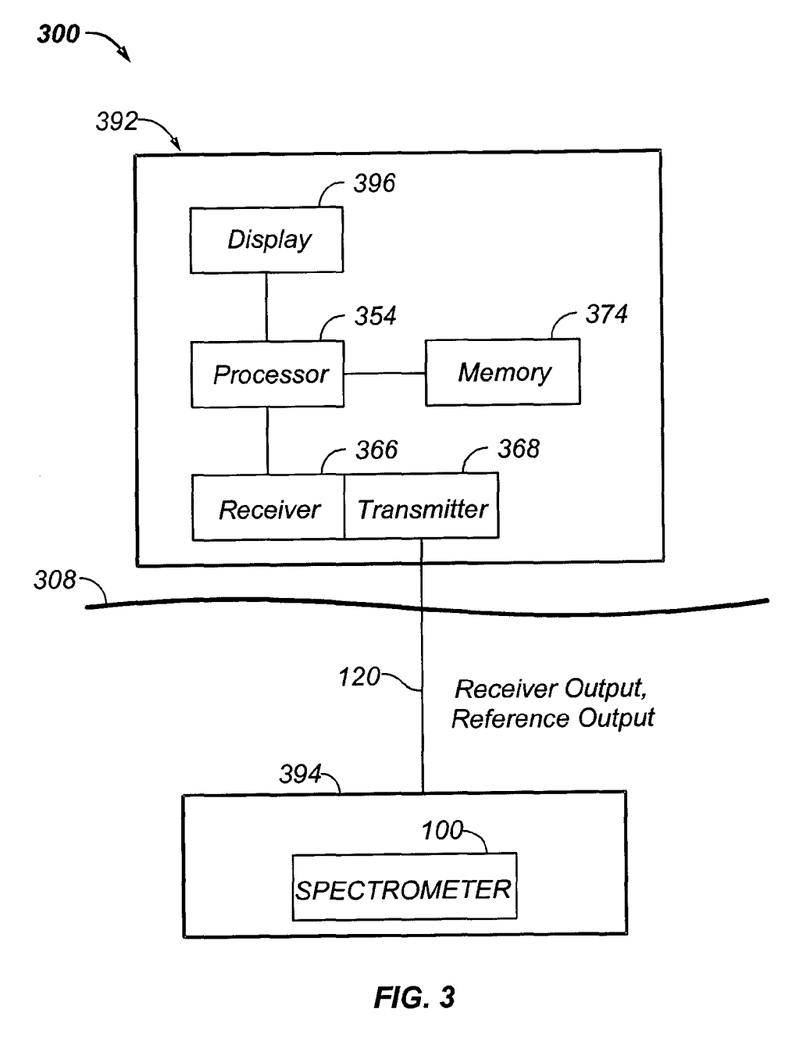
FIG. 3 illustrates a system block diagram according to various embodiments of the invention.

For example, FIG. 3 illustrates a system block diagram according to various embodiments of the invention. Here it can be seen that a system 300 may comprise a number of components, including a logging facility 392.

The logging facility 392, shown located above the surface 308, may comprise a processor 354 and a memory 374 coupled to the processor 354. The memory 374 may comprise instructions which, when executed, result in the system 300 accomplishing any of the methodologies described herein. The processor 354 may include, or be separated from one or more of the processors 124 shown in FIG. 1.

The system 300 may also comprise a housing 394, such as a down hole tool or tool body that is attached to and includes any one or more of the components shown in FIGS. 1-2. Thus, the system 300 can form part of a subsurface exploration system, with a down hole tool used to house various components of the apparatus 100.

The housing 394 may therefore be attached to one or more energy sources (e.g., SC, SC1, SC2 of FIGS. 1-2) and/or one or more sensors (e.g., sensors 116 of FIGS. 1-2), for example. Indeed, any one or more of the components forming a part of the apparatus 100 of FIG. 1, as well as one or more components of the logging facility 392, may be located below the surface 308, perhaps included within the housing 394. Multiple apparatus 100 may be included in the housing 394, as desired. In some cases, the processor 354 is attached to a down hole tool. In some cases, the processor 354 is located at the surface 308, as shown in FIG. 2.

The facility 392 may comprise a receiver 366 and/or transmitter 368 to receive and transmit commands and data to the housing 394, and components located therein. A display 396 may be used display a variety of information, including a material or chemical property of fluids analyzed down hole, as determined by the GSAM.

Figure 4:
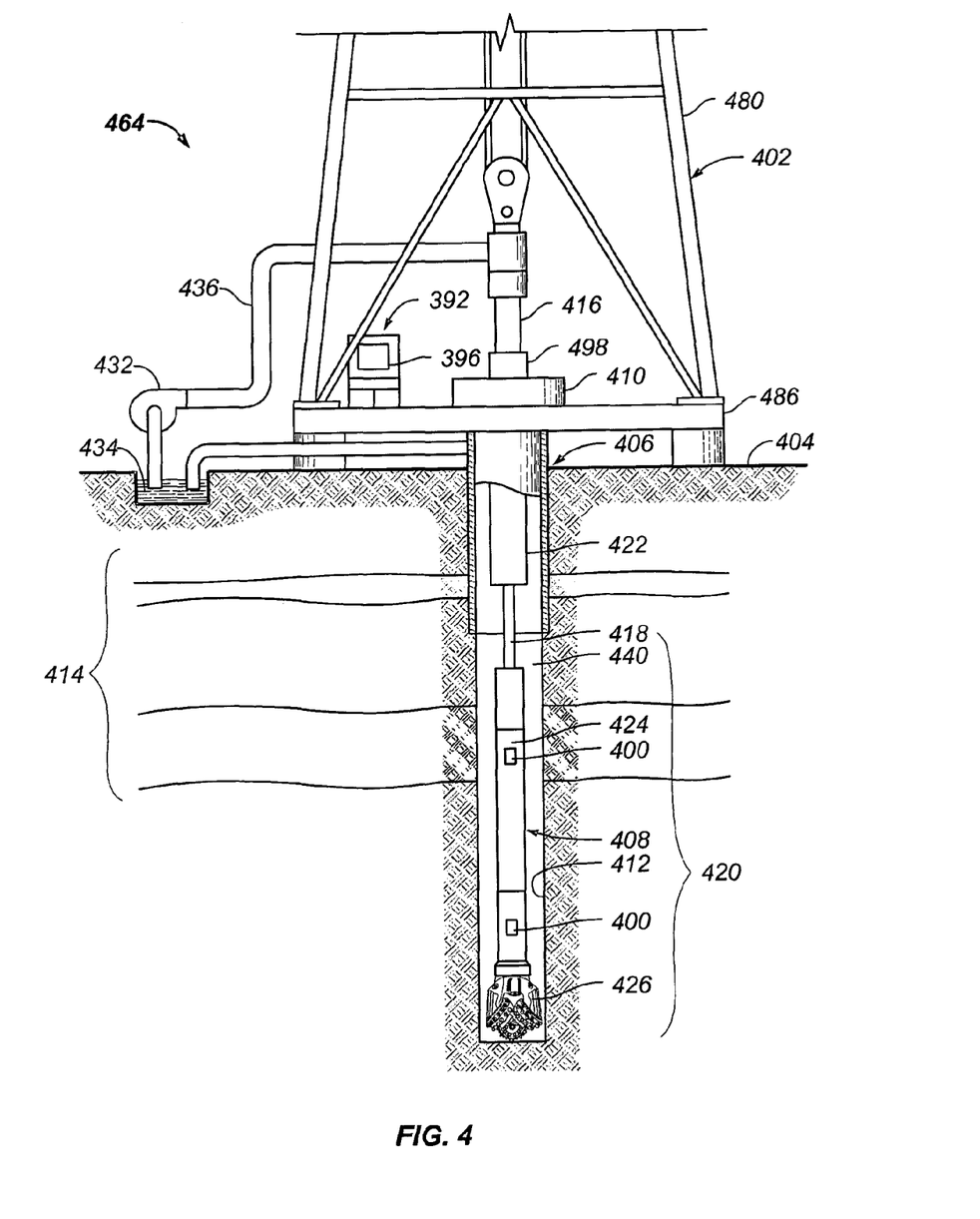
FIGS. 4-5 illustrate additional system embodiments of the invention.
Figure 5:
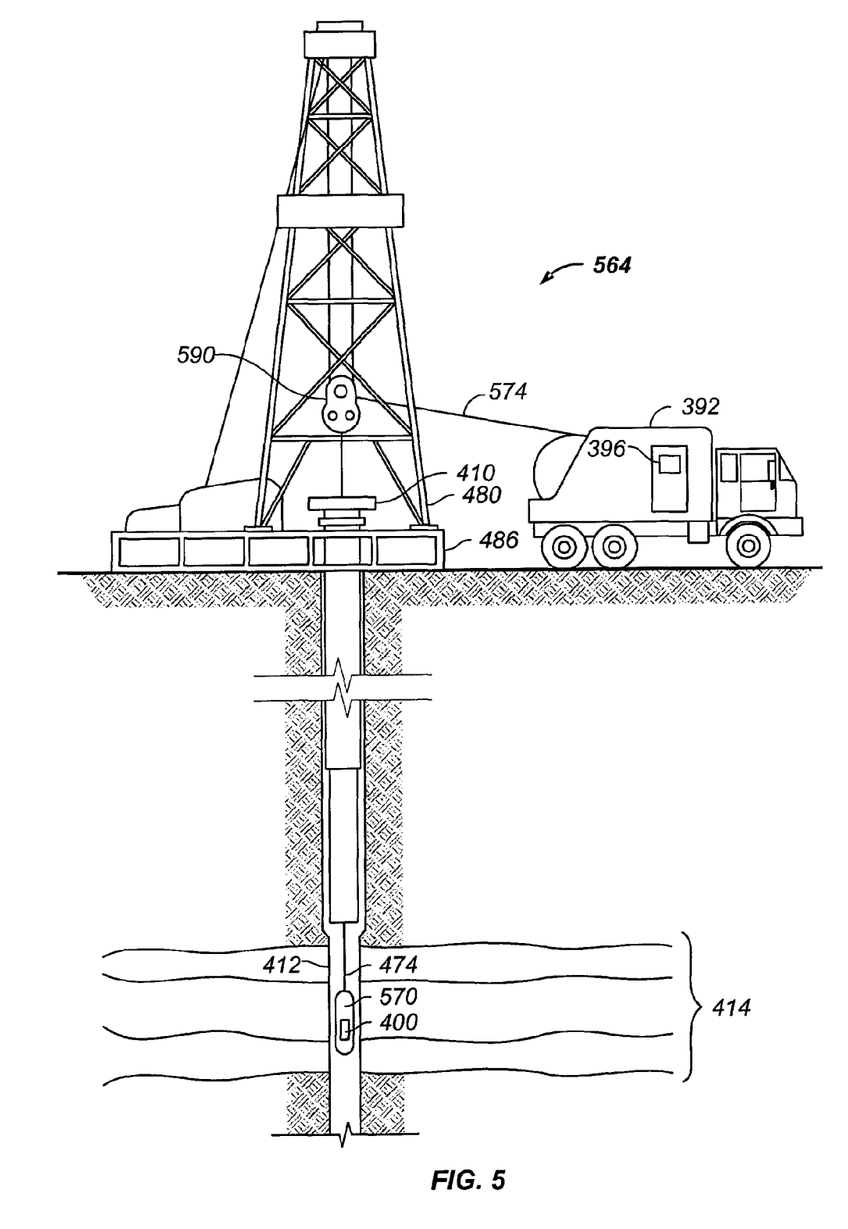

FIGS. 4-5 illustrate additional system embodiments of the invention. For example, FIG. 4 illustrates a system 464 as a drilling rig system embodiment of the invention, and FIG. 5 illustrates a system 564 as a wireline system embodiment of the invention. Thus, systems 464, 564 may comprise portions of a down hole tool 424 as part of a down hole drilling operation, or a tool body 570 as part of a wireline logging operation. The systems 464,564 may each comprise one or more of the systems 300 shown in FIG. 3, as part of the logging facility 392 and/or instruments 400.

Drilling of oil and gas wells is commonly carried out using a string of drill pipes connected together so as to form a drilling string that is lowered through a rotary table 410 into a wellbore or borehole 412. Turning now to FIG. 4, it can be seen how a system 464 may form a portion of a drilling rig 402 located at the surface 404 of a well 406. The drilling rig 402 may provide support for a drill string 408. The drill string 408 may operate to penetrate a rotary table 410 for drilling a borehole 412 through subsurface formations 414. The drill string 408 may include a Kelly 416, drill pipe 418, and a bottom hole assembly 420, perhaps located at the lower portion of the drill pipe 418. In some embodiments, one or more instruments 400, similar to or identical to the system 300 of FIG. 3, may be carried and thus attached to the drill string 408 or the down hole tool 424.

The bottom hole assembly 420 may include drill collars 422, a down hole tool 424, and a drill bit 426. The drill bit 426 may operate to create a borehole 412 by penetrating the surface 404 and subsurface formations 414. The down hole tool 424 may comprise any of a number of different types of tools including MWD (measurement while drilling) tools, LWD (logging while drilling) tools, and others.

During drilling operations, the drill string 408 (perhaps including the Kelly 416, the drill pipe 418, and the bottom hole assembly 420) may be rotated by the rotary table 410. In addition to, or alternatively, the bottom hole assembly 420 may also be rotated by a motor (e.g., a mud motor) that is located down hole. The drill collars 422 may be used to add weight to the drill bit 426. The drill collars 422 may also operate to stiffen the bottom hole assembly 420, allowing the bottom hole assembly 420 to transfer the added weight to the drill bit 426, and in turn, to assist the drill bit 426 in penetrating the surface 404 and subsurface formations 414.

During drilling operations, a mud pump 432 may pump drilling fluid (sometimes known by those of ordinary skill in the art as "drilling mud") from a mud pit 434 through a hose 436 into the drill pipe 418 and down to the drill bit 426. The drilling fluid can flow out from the drill bit 426 and be returned to the surface 404 through an annular area 440 between the drill pipe 418 and the sides of the borehole 412. The drilling fluid may then be returned to the mud pit 434, where such fluid is filtered. In some embodiments, the drilling fluid can be used to cool the drill bit 426, as well as to provide lubrication for the drill bit 426 during drilling operations. Additionally, the drilling fluid may be used to remove subsurface formation 414 cuttings created by operating the drill bit 426.

FIG. 5 shows a well during wireline logging operations. A drilling platform 486 is equipped with a derrick 480 that supports a hoist 590. Here it is assumed that the drilling string has been temporarily removed from the borehole 412 to allow a wireline logging tool body 570, such as a probe or sonde that carries one or more instruments 400, to be lowered by wireline or logging cable 574 into the borehole 412. Typically, the tool body 570 is lowered to the bottom of the region of interest and subsequently pulled upward at a substantially constant speed.

During the upward trip, the instruments 400 included in the tool body 470 may be used to perform measurements in the borehole 412 as they pass by. The measurement data can be communicated to a surface logging facility 392 for storage, processing, and analysis.

The logging facility 392 may be provided with electronic equipment, such any one or more of the components of the system 300 in FIG. 3, including one or more components of the apparatus 100 of FIG. 1.

The systems 464, 564 of FIGS. 4 and 5 may comprise a display 396. The measurement data provided to the facility 392 and displayed on the display 396 may include data similar to that which is gathered and analyzed during drilling operations (e.g., during LWD operations). Such data may include derived data, including material or chemical properties of the fluid 108 used in the apparatus 100 of FIG. 1.

The apparatus 100; flow channel 104; fluid 108; injectors 112; sensors 116; signals 120; processors 124, 354, GSAM*, MCR*; fibers 128, 144; porous media 132; ports 136; detectors 140; devices 148; indicators 152; systems 300, 464, 564; surface 308; processor 354; receiver 366; transmitter 368; memory 374; logging facility 392; display 396; instrument 400; drilling rig 402; well 406; drill string 408;'rotary table 410; borehole 412; formation 414; Kelly 416; drill pipe 418; bottom hole assembly 420; drill collars 422; down hole tool 424; drill bit 426; mud pump 432; mud pit 434; hose 436 systems 464, 564; tool body 470; drilling platform 486; derrick 480; logging cable 574; hoist 590; fluids A1 . . . AN; and energy sources SC, SC1, SC2 may all be characterized as "modules" herein.

Such modules may include hardware circuitry, and/or a processor and/or memory circuits, software program modules and objects, and/or firmware, and combinations thereof, as desired by the architect of the apparatus 100; instruments 400; and systems 300, 464, 564, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 100; instruments 400; and systems 300, 464, 564 are intended to provide a general understanding of the structure of various embodiments, and they are not intended to serve as a complete description of all the elements and features of apparatus and systems that might make use of the structures described herein.

Applications that may incorporate the novel apparatus and systems of various embodiments include a variety of electronic systems, such as televisions, cellular telephones, personal computers, workstations, radios, video players, vehicles, and location technology (e.g., GPS (Global Positioning System) location technology), signal processing for geothermal tools and smart transducer interface node telemetry systems, among others. Some embodiments include a number of methods.

Figure 6:
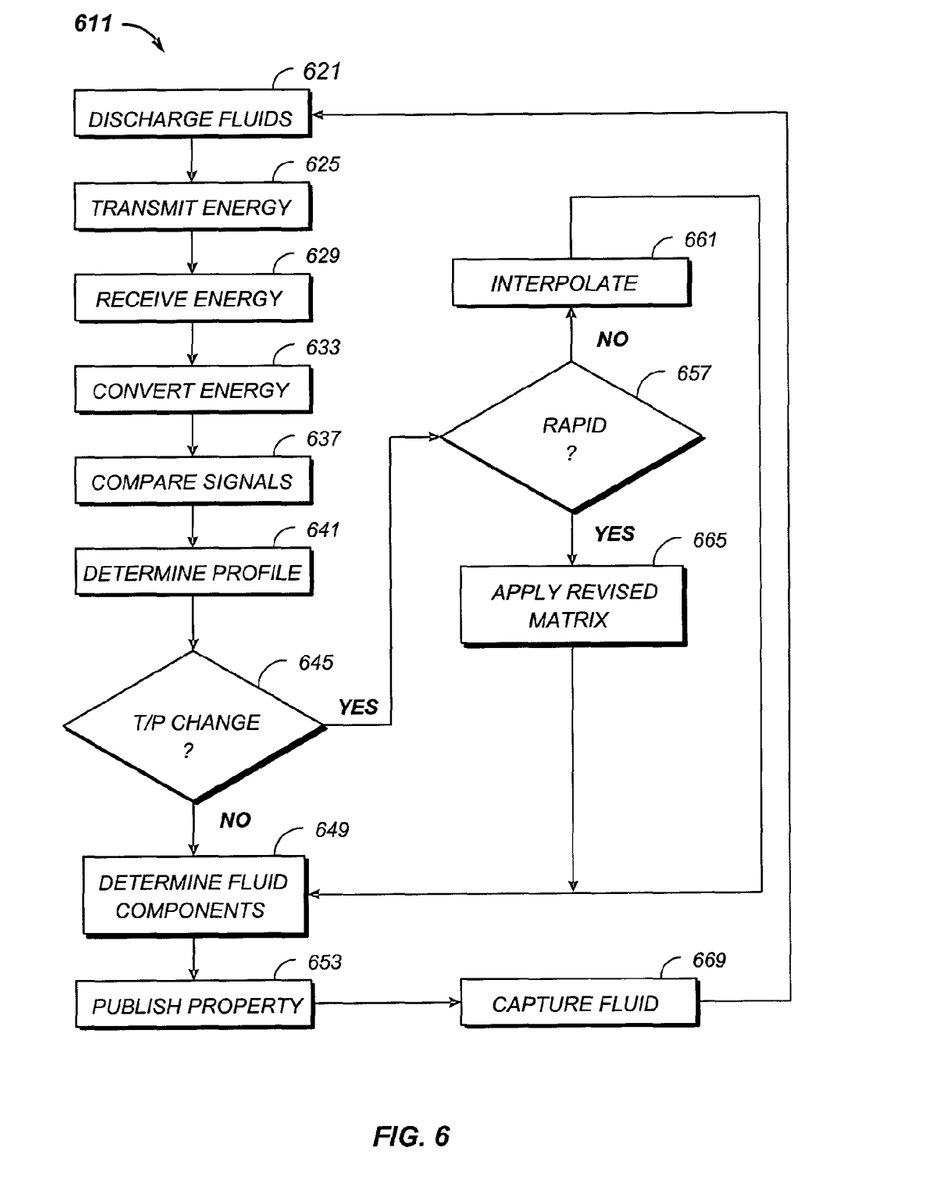
FIG. 6 is a flow diagram illustrating several methods according to various embodiments of the invention.

FIG. 6 is a flow diagram illustrating several methods 611 according to various embodiments of the invention. For example, a processor-implemented method 611 to execute on one or more processors that perform a method to implement GSAM techniques down hole may begin at block 621. The activity at block 621 may include discharging a plurality of spike fluids into a fluid flowing in a flow channel. The method 611 may continue on to block 625 with transmitting energy to the fluid using an energy source coupled to the flow channel.

The method 611 may include receiving, at block 629, downstream from an injection point in the flow channel, the energy modified by the fluid as photometric energy. As described above, a set of orthogonally-independent sensors (e.g., intensity versus wavelength) can provide additional benefits, such as effectively multiplying the actual number of sensors to provide an over-determined GSAM solution. Thus, the activity at block 629 may further comprise receiving the energy using a set of orthogonally-independent sensors.

The method 611 may go on to include, at block 633, converting the photometric energy to at least one photometric signal.

The method 611 may further include comparing the at least one photometric signal with a reference signal to determine at least one photometric property of the fluid at block 637. The reference signal may comprise an absolute reference signal associated with the energy transmitted into the fluid (i.e., a reference signal undisturbed by photometric interaction with the spiked fluid), or a relative reference signal associated with a photometric signal that was previously received (i.e., a change in the received photometric signal interacting with the spiked fluid over time), or both.

As noted above, MCR techniques can be used to better determine the concentration profile of the spike fluids over time, enhancing the accuracy of the GSAM result. As used herein, MCR is defined as a group of techniques which help resolve mixtures by determining the number of constituents, their response profiles (spectra, pH profiles, time profiles, elution profiles) and their estimated concentrations, when no prior information is available about the nature and composition of these mixtures.

A flexible two-way data analysis method based on the assumption of Lambert-Beer's Law, MCR decomposes the experimental data matrix D into the product of two smaller matrices C and $S^T$, with C being a matrix of concentration profiles for each modeled component in the system, and S being the matrix of the corresponding pure spectra: $D=CS^T+E$. In the case of the processes described herein, D corresponds to the response matrix for the sensor array, C corresponds to the concentration of the individual components, $S^T$ corresponds to the sensor array response to individual components, and E corresponds to the inherent error of the system.

The number of components (chemical species) contributing to D and to be modeled by MCR are determined, and initial estimates for C or $S^T$ are provided. Then C and $S^T$ can be optimized iteratively in an Alternating Least Squares (ALS) algorithm until convergence is reached. Diverse constraints (non-negativity, unimodality, selectivity, closure . . . ) can be applied during the iterations in order to obtain a physically and/or chemically meaningful solution.

Thus, the method 611 may comprise, at block 641, determining a concentration profile of the plurality of spike fluids in the flow channel as a function of time using MCR, so that the profile can be provided to the GSAM (as part of the activity that occurs at block 649) to refine the determination of the fluid components that results from the use of the GSAM.

Slow changes in fluid temperature and pressure can be handled via interpolation between GSAM application cycles. Thus, if there is a change in pressure and/or temperature between GSAM cycles, as determined at block 645, the method 611 may comprise determining whether the change is slow or rapid, as compared to some selected period of time. That is, if the change takes longer to occur than the time period selected, than it can be classified as a "slow" change. However, if the change occurs more quickly than the selected time period, then the change may be classified as "rapid".

Therefore, the method 611 may include, at block 657, detecting that at least one of a temperature change or a pressure change has occurred over a period of time that is longer than a selected time window (e.g., the change is slow) and, at block 661, interpolating response factors arising out of the GSAM between individual GSAM determination cycles.

Rapid changes in fluid temperature and pressure can be addressed by using a revised response factor matrix. Therefore, the method 611 may also include, at block 657, detecting that at least one of a temperature change or a pressure change has occurred over a period of time that is shorter than a selected time window and, at block 665, applying a revised response factor matrix as part of the GSAM up to a point in time approximately coinciding with a time included in the selected time window.

The change in the response indicated by the sensors in the fluid flow is used by GSAM to determine components in the fluid. Thus, the method 611 includes, at block 649, determining at least one component of the fluid using the at least one photometric property supplied to the GSAM. The activity at block 649 may further include using mathematical deconvolution methods such as MCR, principal component analysis, or eigenvector methods to derive an end member corrected response where end members comprise both the spiked fluids as well as the formation fluid. In some embodiments, the activity at block 649 includes capturing an initial pump out fluid assumed to be 100% contamination and using at least some of the initial pump out fluid as an injection spike fluid throughout a portion of a pump out operation to calculate contamination level by GSAM.

In some embodiments, there is no optical energy transmitted into the fluid, and the spike response properties are monitored by multiple sensors, including non-optical sensors, such as pH sensors, specific chemical element sensors, etc.

In an elementary form then, the method 611 may comprise comparing the photometric signal from the fluid with a reference signal to determine a photometric property of the fluid, which in turn is used to determine a component of the fluid using the GSAM method. That is, using GSAM in down hole environments may involve adding standard mixtures to a fluid and deconvolving the response of an array of detectors so that the change in detector response is normalized to the sensor and fluid matrix. This process may be applied to any set of detectors which vary in a substantially linear fashion with respect to the addition, regardless of the sensor type. Therefore GSAM may be applied using optical response data, contamination data, other data, and/or combinations thereof.

Many fluid components can be determined using GSAM in down hole environments. These include, among others, the gas-oil ratio (GOR), saturates, aromatics, resins, asphaltenes, esters, olefins, and/or contamination.

The properties of the fluid being sampled in the channel can be determined based on the received intensity of the photometric energy, as compared with the reference, and published to a display, memory, or printer. Thus, the method 611 may go on to include, at block 653, publishing the identity of the at least one component as a material property or a chemical property of the fluid.

The method 611 may further include refinements that can improve the sampling accuracy of the sensors. For example, a sample of the flowing fluid, including a contaminant (the sample may be assumed to comprise 100% contamination in some embodiments), can be used as one of the spike fluids to further refine the composition determination. Thus, the method 611 may include capturing a portion of the fluid flowing in the channel, and injecting some of the fluid into the flow channel as part of the activity at block 669.

It should be noted that the methods described herein do not have to be executed in the order described, or in any particular order. Moreover, various activities described with respect to the methods identified herein can be executed in iterative, serial, or parallel fashion. Some activities described for one method may be added to another, and some of the included activities may be left out. Information, including parameters, commands, operands, and other data, can be sent and received in the form of one or more carrier waves.

Figure 7:
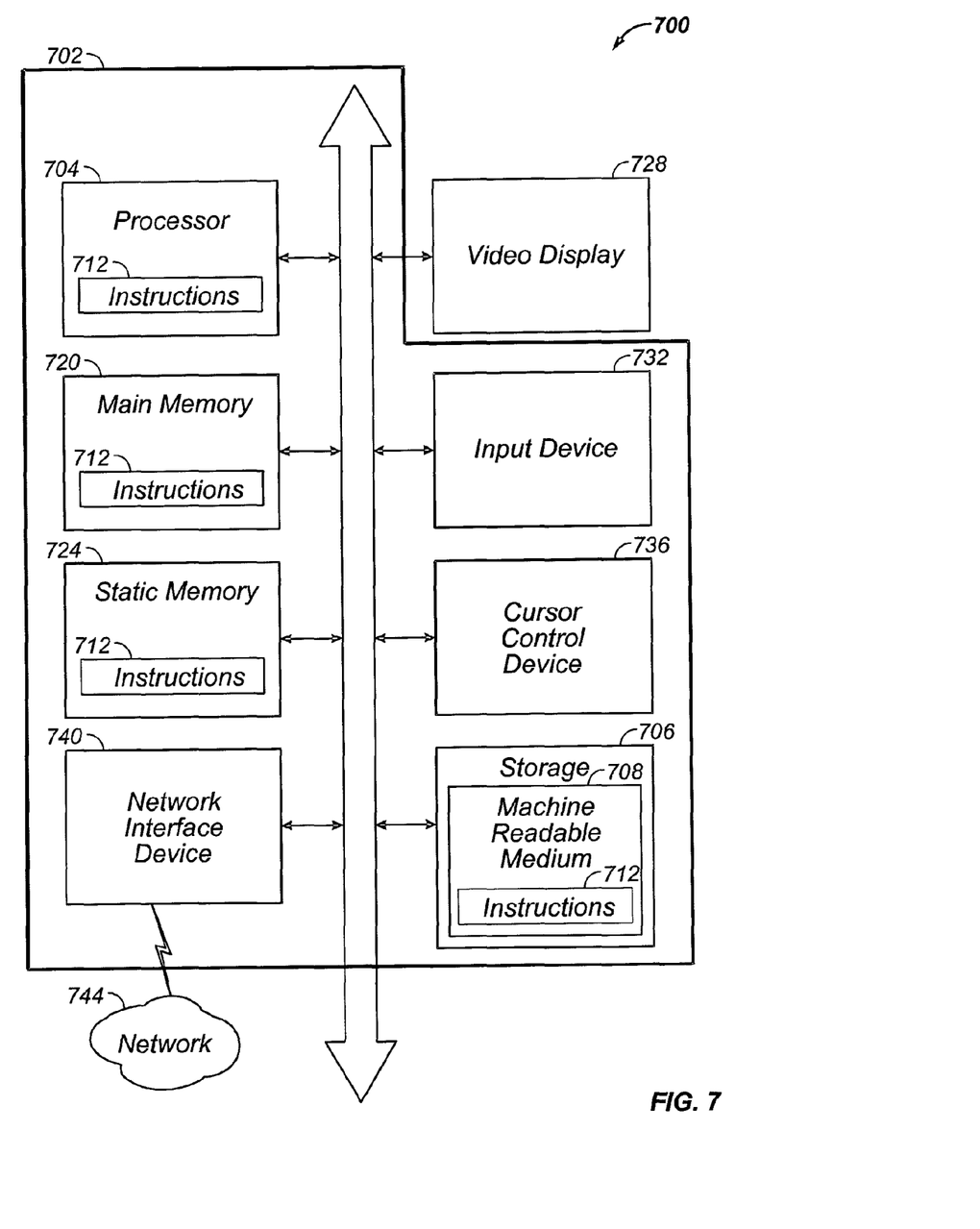
FIG. 7 is a block diagram of an article according to various embodiments of the invention.

FIG. 7 is a block diagram of an article 700 of manufacture, including a specific machine 702, according to various embodiments of the invention. Upon reading and comprehending the content of this disclosure, one of ordinary skill in the art will understand the manner in which a software program can be launched from a computer-readable medium in a computer-based system to execute the functions defined in the software program.

One of ordinary skill in the art will further understand the various programming languages that may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those of ordinary skill in the art, such as application program interfaces or interprocess communication techniques, including remote procedure calls. The teachings of various embodiments are not limited to any particular programming language or environment. Thus, other embodiments may be realized.

For example, an article 700 of manufacture, such as a computer, a memory system, a magnetic or optical disk, some other storage device, and/or any type of electronic device or system may include one or more processors 704 coupled to a machine-readable medium 708 such as a memory (e.g., removable storage media, as well as any memory including an electrical, optical, or electromagnetic conductor comprising tangible media) having instructions 712 stored thereon (e.g., computer program instructions), which when executed by the one or more processors 704 result in the machine 702 performing any of the actions described with respect to the processes or methods described above.

The machine 702 may take the form of a specific computer system having a processor 704 coupled to a number of components directly, and/or using a bus 716. Thus, the machine 702 may be similar to or identical to the system 300 in FIG. 3, or the logging facility 392 shown in FIGS. 3-5.

Turning now to FIG. 7, it can be seen that the components of the machine 702 may include main memory 720, static or non-volatile memory 724, and mass storage 706. Other components coupled to the processor 704 may include an input device 732, such as a keyboard, or a cursor control device 736, such as a mouse. An output device 728, such as a video display, may be located apart from the machine 702 (as shown), or made as an integral part of the machine 702.

A network interface device 740 to couple the processor 704 and other components to a network 744 may also be coupled to the bus 716. The instructions 712 may be transmitted or received over the network 744 via the network interface device 740 utilizing any one of a number of well-known transfer protocols (e.g., HyperText Transfer Protocol). Any of these elements coupled to the bus 716 may be absent, present singly, or present in plural numbers, depending on the specific embodiment to be realized.

The processor 704, the memories 720, 724, and the storage device 706 may each include instructions 712 which, when executed, cause the machine 702 to perform any one or more of the methodologies described herein. In some embodiments, the machine 702 operates as a standalone device or may be connected (e.g., networked) to other machines. In a networked environment, the machine 702 may operate in the capacity of a server or a client machine in server-client network environment, or as a peer machine in a peer-to-peer (or distributed) network environment.

The machine 702 may comprise a personal computer (PC), a workstation, a tablet PC, a set-top box (STB), a PDA, a cellular telephone, a web appliance, a network router, switch or bridge, server, client, or any specific machine capable of executing a set of instructions (sequential or otherwise) that direct actions to be taken by that machine to implement the methods and functions described herein. Further, while only a single machine 702 is illustrated, the term "machine" shall also be taken to include any collection of machines that individually or jointly execute a set (or multiple sets) of instructions to perform any one or more of the methodologies discussed herein.

While the machine-readable medium 708 is shown as a single medium, the term "machine-readable medium" should be taken to include a single medium or multiple media (e.g., a centralized or distributed database, and/or associated caches and servers, and or a variety of storage media, such as the registers of the processor 704, memories 720, 724, and the storage device 706 that store the one or more sets of instructions 712. The term "machine-readable medium" shall also be taken to include any medium that is capable of storing, encoding or carrying a set of instructions for execution by the machine and that cause the machine 702 to perform any one or more of the methodologies of the present invention, or that is capable of storing, encoding or carrying data structures utilized by or associated with such a set of instructions. The terms "machine-readable medium" or "computer-readable medium" shall accordingly be taken to include tangible media, such as solid-state memories and optical and magnetic media.

Various embodiments may be implemented as a stand-alone application (e.g., without any network capabilities), a client-server application or a peer-to-peer (or distributed) application. Embodiments may also, for example, be deployed by Software-as-a-Service (SaaS), an Application Service Provider (ASP), or utility computing providers, in addition to being sold or licensed via traditional channels.

Using the apparatus, systems, and methods disclosed, those in the petroleum recovery industry and other industries may now be able to determine spectroscopic properties of various sampled materials more readily when harsh environmental conditions are present. The analyses conducted may thus benefit from results that are obtained with increased accuracy and efficiency.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:
   a flow channel to contain a flow of fluid;
   a plurality of fluid injectors to discharge a corresponding plurality of spike fluids into the flow channel;
   at least one energy source coupled to the flow channel to direct energy into the fluid;
   at least one sensor coupled to the flow channel downstream from the plurality of fluid injectors, the at least one sensor to receive the energy modified by the fluid as photometric energy and to provide a signal indicating a property of the photometric energy; and
   a processor to acquire the signal and to determine a material or chemical property of the fluid using a generalized standard addition method.

2. The apparatus of claim 1, further comprising:
   a porous medium to mix the fluid, the porous medium disposed within the flow channel upstream or downstream from the plurality of fluid injectors.

3. The apparatus of claim 1, wherein the at least one energy source and the at least one sensor are disposed in a substantially radial arrangement around a periphery of the flow channel.

4. The apparatus of claim 1, wherein the at least one energy source comprises a broadband energy source, and wherein the at least one sensor comprises:
   one of a tunable sensor to resolve a plurality of wavelengths in the photometric energy or a plurality of sensors corresponding to a plurality of reception wavelength sensitivities.

5. The apparatus of claim 1, wherein the at least one energy source comprises:
   one of a broadband source or a substantially monochromatic source.

6. The apparatus of claim 1, wherein the energy source comprises:
   one of a single broadband source or a plurality of substantially monochromatic sources to provide the energy, wherein the energy comprises a corresponding plurality of energies directed to the fluid, the corresponding plurality of energies to be received in a modified form by a corresponding plurality of sensors that include the at least one sensor.

7. The apparatus of claim 1, further comprising:
   a reference detector; and
   a bypass fiber to couple the energy source to the reference detector.

8. The apparatus of claim 1, further comprising:
   at least one optical fiber to couple the at least one sensor to at least one optical port in the flow channel.

9. The apparatus of claim 1, wherein the at least one sensor comprises one of a liquid crystal diode (LCD) element; a charge-coupled device (CCD) element; complementary metal-oxide semiconductor (CMOS) elements; band-gap, silicon, and/or infrared photodiodes; thermal detectors; and/or combinations of these.

10. The apparatus of claim 1, wherein the at least one energy source comprises at least one light-emitting diode (LED).

11. A system, comprising:
a flow channel to contain a flow of fluid;
a plurality of fluid injectors to discharge a corresponding plurality of spike fluids into the flow channel;
at least one energy source coupled to the flow channel to direct energy into the fluid;
at least one sensor coupled to the flow channel downstream from the plurality of fluid injectors, the at least one sensor to receive the energy modified by the fluid as photometric energy and to provide at least one signal indicating a property of the photometric energy;
a processor to acquire the at least one signal and to determine a material or chemical property of the fluid using a generalized standard addition method (GSAM); and
a downhole tool attached to the energy source.

12. The system of claim 11, wherein the processor is attached to the downhole tool.

13. The system of claim 11, wherein the at least one energy source comprises a first number of visible wavelength emission devices, and wherein the at least one sensor comprises a second number of different types of detectors to provide an effective number of sensors equal to the first number multiplied by the second number.

14. The system of claim 11, further comprising:
at least one of a heating device or a cooling device to control a temperature of the fluid contained in the flow channel.

15. The system of claim 11, further comprising:
at least one of a pressure indicator or a temperature indicator to indicate a fluid matrix condition that initiates application of a revised response factor matrix as part of the GSAM.

16. The system of claim 11, further comprising:
a reference sensor to receive the energy unmodified by interaction with the fluid.

17. A method, comprising:
discharging a plurality of spike fluids into a fluid flowing in a flow channel;
transmitting energy to the fluid using an energy source coupled to the flow channel;
receiving, downstream from an injection point in the flow channel, the energy modified by the fluid as photometric energy;
converting the photometric energy to at least one photometric signal;
comparing the at least one photometric signal with a reference signal to determine at least one photometric property of the fluid; and
determining at least one component of the fluid using the at least one photometric property supplied to a generalized standard addition method (GSAM).

18. The method of claim 17, further comprising:
publishing an identity of the at least one component as a material property or a chemical property of the fluid.

19. The method of claim 17, further comprising:
detecting that at least one of a temperature change or a pressure change has occurred over a period of time that is longer than a selected time window; and
interpolating response factors arising out of the GSAM between individual GSAM determination cycles included in the determining.

20. The method of claim 17, further comprising:
detecting that at least one of a temperature change or a pressure change has occurred over a period of time that is shorter than a selected time window; and
applying a revised response factor matrix as part of the GSAM up to a point in time approximately coinciding with a time included in the selected time window.

21. The method of claim 17, further comprising:
determining a concentration profile of the plurality of spike fluids in the flow channel as a function of time using multivariate curve resolution (MCR); and
providing the profile to the GSAM to refine the determining of the at least one component of the fluid.

22. The method of claim 17, further comprising:
capturing a portion of the fluid; and
injecting some of the fluid into the flow channel.

23. The method of claim 17, wherein the reference signal comprises:
one of an absolute reference signal associated with the energy transmitted into the fluid or a relative reference signal associated with a prior photometric signal.

24. The method of claim 17, wherein the receiving further comprises:
receiving the energy using a set of orthogonally-independent sensors.

25. The method of claim 17, wherein the at least one component of the fluid comprises one or more of a gas-oil ratio, a saturate, an aromatic, a resin, an asphaltene, an ester, an olefin, or a contamination.

26. The method of claim 17, further comprising:
capturing an initial pump out fluid assumed to be 100% contamination and using at least some of the initial pump out fluid as an injection spike fluid throughout a portion of a pump out operation to calculate contamination level by the GSAM.

* * * * *